(12) United States Patent
Jones

(10) Patent No.: US 10,470,699 B2
(45) Date of Patent: Nov. 12, 2019

(54) METHOD AND SYSTEM FOR DETECTING PANCREATIC TRAUMA

(71) Applicant: Mark W. Jones, East Lansing, MI (US)

(72) Inventor: Mark W. Jones, East Lansing, MI (US)

(*) Notice: Subject to any disclaimer, the term of this patent is extended or adjusted under 35 U.S.C. 154(b) by 154 days.

(21) Appl. No.: 15/635,854

(22) Filed: Jun. 28, 2017

(65) Prior Publication Data

US 2018/0000404 A1    Jan. 4, 2018

Related U.S. Application Data

(60) Provisional application No. 62/357,514, filed on Jul. 1, 2016.

(51) Int. Cl.
| | | |
|---|---|---|
| *A61B 5/00* | (2006.01) | |
| *A61K 49/00* | (2006.01) | |
| *A61B 5/145* | (2006.01) | |
| *A61B 5/1473* | (2006.01) | |
| *A61F 13/36* | (2006.01) | |
| *C12Q 1/40* | (2006.01) | |
| *G01N 33/52* | (2006.01) | |

(52) U.S. Cl.
CPC .......... *A61B 5/425* (2013.01); *A61B 5/14546* (2013.01); *A61B 5/14735* (2013.01); *A61B 5/4283* (2013.01); *A61F 13/36* (2013.01); *A61K 49/006* (2013.01); *A61K 49/0069* (2013.01); *C12Q 1/40* (2013.01); *G01N 33/528* (2013.01); *A61B 2505/05* (2013.01); *A61B 2562/0295* (2013.01)

(58) Field of Classification Search
CPC . A61B 5/425; A61B 5/14546; A61B 5/14735; A61B 5/4283; A61B 2505/05; A61B 2562/0295; C12Q 1/40; G01N 33/528; A61K 49/0069; A61K 49/006; A61F 13/36
See application file for complete search history.

(56) References Cited

U.S. PATENT DOCUMENTS 2,597,011 A * 5/1952 Hoaglund ............... A61L 15/28
                                                      106/122
3,419,136 A * 12/1968 Pratt ...................... A61F 15/001
                                                      206/361
(Continued)

OTHER PUBLICATIONS

Chemocare, "Hyperamylasemia (High Blood Amylase Level)", Dec. 27, 2012, https://web.archive.org/web/20121227072307/http://chemocare.com/chemotherapy/side-effects/hyperamylasemia-high-amylase.aspx (Year: 2012).*

(Continued)

*Primary Examiner* — Eric F Winakur
*Assistant Examiner* — Abid A Mustansir
(74) *Attorney, Agent, or Firm* — Gardner, Linn, Burkhart & Ondersma LLP

(57) ABSTRACT

A method and system are provided for detecting pancreatic trauma in a trauma patient during a surgical operation. The method includes positioning a detection device in contact with the patient's pancreas, applying a chemical indicator to the detection device after removing the detection device from the patient, and detecting a chemical reaction on the detection device that is indicative of the pancreas releasing an enzyme as a result of pancreatic trauma.

16 Claims, 2 Drawing Sheets

(56) References Cited

U.S. PATENT DOCUMENTS

| | | | | |
|---|---|---|---|---|
| 4,729,948 A | * | 3/1988 | Saruhashi | C12Q 1/40 435/22 |
| 2008/0315018 A1 | * | 12/2008 | Withers | B05B 11/0037 239/526 |

OTHER PUBLICATIONS

Webexhibits, "Do It Yourself: Starch Test", Jun. 25, 2010, https://web.archive.org/web/20100625231926/http://www.webexhibits.org/causesofcolor/6AC.html (Year: 2010).*

"Experiment 10—Enzymes". 2010, https://laney.edu/cheli-fossum/wp-content/uploads/sites/210/2012/01/10-Enzymes.pdf (Year: 2012).*

* cited by examiner

METHOD AND SYSTEM FOR DETECTING PANCREATIC TRAUMA

CROSS REFERENCE TO RELATED APPLICATION

The present application claims the filing benefits of U.S. provisional application Ser. No. 62/357,514, filed Jul. 1, 2016, which is hereby incorporated herein by reference in its entirety.

FIELD OF THE INVENTION

The present invention is directed to a method and a system for diagnosing injury to a pancreas during a surgical procedure.

BACKGROUND OF THE INVENTION

The pancreas is a critical organ that performs both endocrine and exocrine functions. It produces insulin and the enzymes amylase and lipase. In particular, lipase is involved with the breakdown of fats and amylase breaks down starch. Internal organs such as the pancreas can easily be injured in a trauma. These injuries, whether penetrating or blunt, may be difficult for a trauma surgeon to detect. Missed pancreatic injuries can be devastating, resulting in a patient's delayed morbidity and possible mortality. A trauma surgeon makes every effort to avoid missed pancreatic damage, but these injuries are often missed at the time of a diagnostic operation, or laparotomy. Significant pancreatic duct disruptions that result from pancreatic trauma may yield merely subtle or no visual findings at surgery, yet damage to the pancreas will generally result in the release of amylase and/or lipase outside of the enteric system due to disruption of the pancreatic duct or damage to the parenchyma.

There are several devices and methods available to evaluate a patient's pancreas after suffering trauma. The most commonly used and accurate test is a CAT scan directed at the pancreas with an IV and/or an orally administered contrast. Despite much research to develop devices and methods for detecting pancreatic injury, common tests require significant time and expense to complete, and also have a significant false-negative rate.

SUMMARY OF THE INVENTION

The present invention provides a method and device or system for detecting pancreatic trauma in a patient during a surgical operation. The method includes positioning a detection device in contact with the patient's pancreas, applying a chemical indicator to the detection device after removing the detection device from the patient, and detecting (by visual observation) a chemical reaction on the detection device that is indicative of the pancreas releasing an enzyme as a result of trauma.

In one form of the present invention, the detection device is a surgical pad or sponge that is impregnated or coated with a starch, while the chemical indicator is an iodine-based solution or the like, such as Betadine®.

Because the difficulty of detecting pancreatic trauma may vary, the method is customizable to increase the likelihood, consistency, and accuracy of detecting a reaction that is indicative of enzyme release caused by injury to the patient's pancreas. Thus, the method may include determining a desired concentration of the starch, based on the patient type and/or based on the chemical indicator. The method may further include determining a concentration of the iodine-based solution based on the patient type, based on the detection device and/or based on the starch or starch concentration.

Optionally a kit may be provided, the kit containing two or more detection devices having the same or different starches or starch-like substances or starch concentrations, and/or two or more chemical indicators having the same or different iodine or iodine-like substances or iodine concentrations. Thus, a surgeon or other medical professional may select the desired combination of detection device and chemical indicator from the kit for use on a particular trauma patient.

Thus, the present invention provides a method for detecting pancreatic injuries during a surgical operation on a trauma patient. The early detection of such an injury facilitates the early treatment of the pancreatic injury in a trauma patient during the surgical operation.

These and other objects, advantages, purposes and features of this invention will become apparent upon review of the following specification in conjunction with the drawings.

DESCRIPTION OF THE PREFERRED EMBODIMENTS

Figure 1:
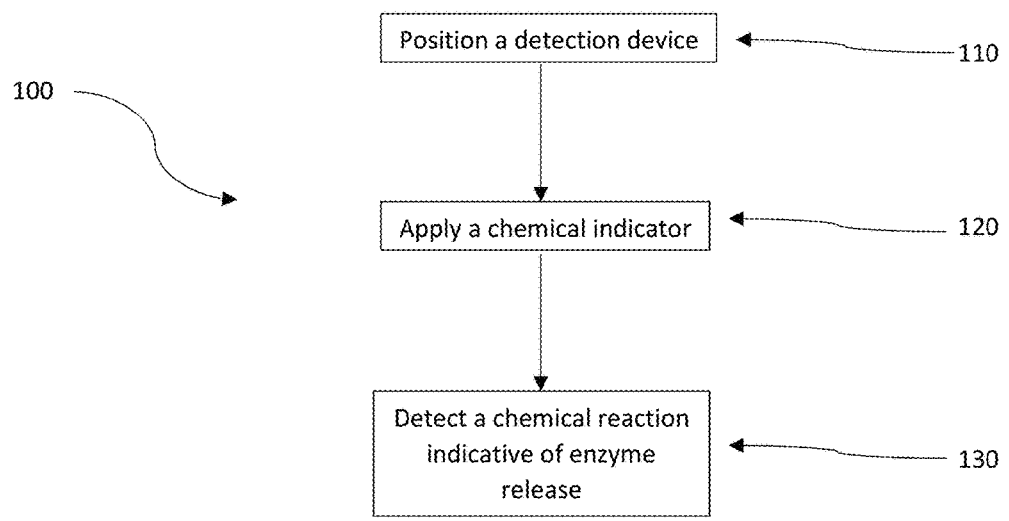
FIG. 1 is a flowchart depicting a method of detecting pancreatic trauma in accordance with the present invention.
Figure 2:
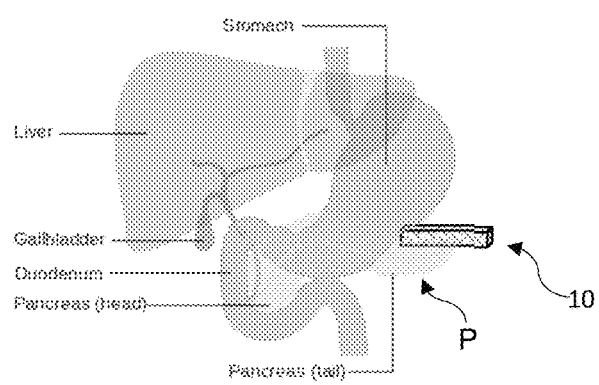
FIG. 2 is a schematic of a detection device positioned in contact with a patient's pancreas, according to the method depicted in FIG. 1.
Figure 3:
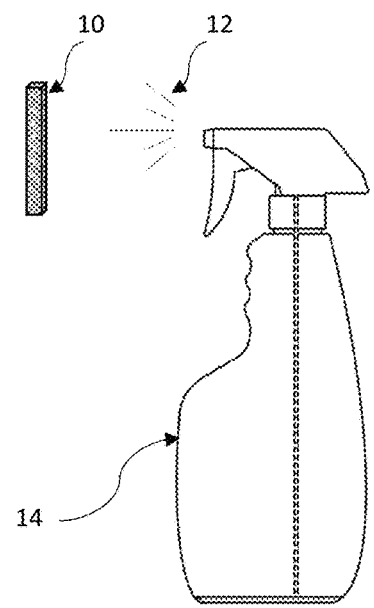
FIG. 3 is a schematic depicting the application of a chemical indicator to the detection device by an applicator, according to the method depicted in FIG. 1.

Referring now to the drawings and the illustrative embodiments depicted therein, a method 100 for detecting pancreatic trauma includes positioning 110 a detection device 10 in contact with a trauma patient's pancreas during a surgical operation, applying 120 a chemical indicator 12 to the detection device 10, and detecting 130 a chemical reaction that is indicative of enzyme release caused by trauma (FIGS. 1-3). In the illustrated embodiment of FIGS. 2 and 3, the detection device 10 is a starch-impregnated absorbent sponge or surgical pad, such as a Telfa®-brand surgical pad. An operator, such as a surgeon, places the detection device 10 in contact with a patient's surgically-exposed pancreas P or surrounding tissues and fluids, such as during a laparotomy. Detection device 10 is preferably made from a deformable material, such as the sponge or surgical pad referenced above, to facilitate its insertion into (and removal from) a patient's body cavity.

If there has been a significant injury to the pancreas P during a trauma event, such as an injury causing a disruption of the pancreatic duct or damage to the pancreatic parenchyma, enzymes will typically seep from the patient's enteric system and onto the detection device 10 that is placed in contact with the pancreas P and/or its secretions. The secretions from the pancreas P contain enzymes, including amylase or lipase. Positioning 110 the detection device 10 into contact with the injured pancreas P and/or surrounding tissues and fluids (FIG. 2) causes the detection device 10 to contact these enzymes, of which amylase will hydrolyze or break down the starch that is coated or impregnated into the detection device 10.

Applying 120 a chemical indicator 12 onto the detection device 10 (FIG. 3) will cause a chemical reaction on the detection device 10 that results in a visual indication on the detection device 10. In other words, the chemical indicator 12, when combined with the starch present on the detection device 10, will produce a different color on any areas of the detection device 10 in which starch has been hydrolyzed, thus providing a visual indication that there is amylase present outside the pancreas P, and thus indicating a traumatic injury to the pancreas P.

In the present embodiment, the chemical indicator 12 is an iodine-based product, such as Betadine® (which contains povidone-iodine), or other iodine-based solution. The chemical indicator 12 can be applied to the detection device 10 using various techniques, such as by a spray bottle 14 (FIG. 3) or other liquid dispenser, for example, or by directly applying in another manner. Detecting 130 the visual indication may depend on many variables, including the chemical indicator 12 solution and its concentration, the type of starch of the detection device 10 and its concentration, and the length of contact time of the detection device 10 to the pancreatic enzyme(s). Thus, applying 120 the chemical indicator 12 may provide a starch-chemical indicator reaction at a localized area of detection device 10, or along substantially the entire outer surface of detection device 10, as further described below.

Betadine® is generally brown-colored, but becomes generally violet-colored when it contacts a starch, such as the starch that is impregnated into the detection device 10. Therefore, applying 120 the chemical indicator 12 to an outer surface of the detection device 10 will cause the detection device 10 to become generally violet-colored in areas where starch is still present, and will generally become brown-colored in areas where starch is no longer present due to hydrolyzing or breaking down of the starch by amylase. Thus, areas of the detection device 10 that have contacted amylase released from an enzyme-releasing pancreas P (i.e., an injured pancreas) will become generally brown-colored when sprayed with the iodine-based chemical indicator 12. However, areas of the detection device 10 that have contacted only an un-injured pancreas P and/or nearby tissues or fluids, will become generally violet-colored as a result of the starch-chemical indicator reaction. Detecting 130 the reaction that is indicative of enzyme release thus includes visually observing the detection device 10.

The method 100 is customizable to increase the likelihood of detecting a reaction that is indicative of enzyme release. The pancreatic parenchyma of a given patient type may be expected to emit different amounts of enzyme-containing fluid when injured. For example, most human pancreas will release less amylase or lipase than will be released by other mammals, such as dogs. Therefore, the method 100 may be customized to account for varying concentrations of amylase or lipase for detecting the starch-chemical indicator reaction.

Figure 4:
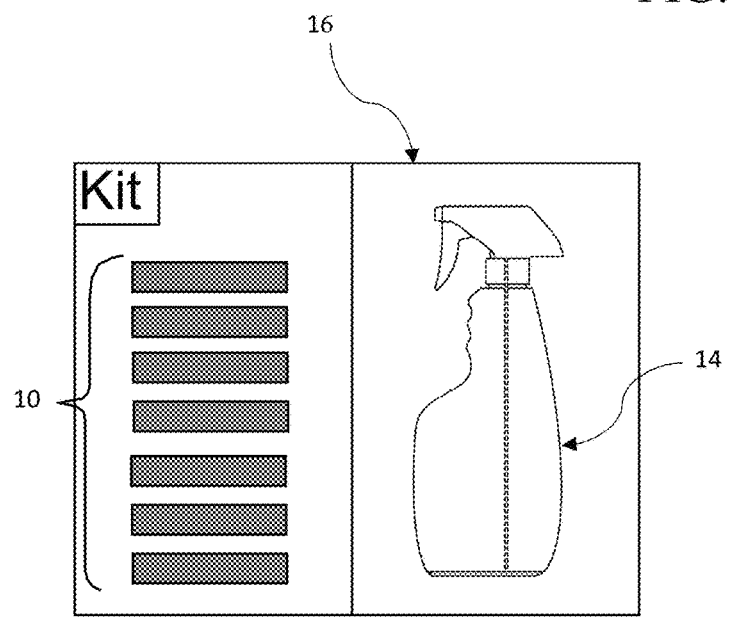
FIG. 4 is a schematic view of a pancreatic trauma detection kit in accordance with the present invention.

For example, a set of detection devices 10 may have varying concentrations of starch impregnated and dried into each detection device 10 in a manner that reduces the likelihood of false positive indications due to the small amount of amylase that humans may typically secrete without any pancreatic trauma. Thus, the method includes selecting a desired detection device 10 from a set of detection devices having different concentrations of starch, according to patient type, so as to reduce or preclude the chances of a false positive indication, while maintaining a high likelihood of a true positive indication or true negative indication. In addition, the chemical indicator 12 may be a solution that is one of many concentrations of Betadine® or another iodine-based solution. Furthermore, an operator may vary the time that the detection device 10 is in contact with the patient's pancreas P, which may increase the likelihood, consistency, and accuracy of detecting a reaction that is indicative of enzyme release. Therefore, the method 10 may further include calibrating the result of the reaction according to previously-determined visual indications for various concentrations of chemical indicators 12 and/or starches of the detection device 10. Optionally, a set of detection devices 10 and a set of chemical indicators 12 may be provided in the form of a kit 16 (FIG. 4), which may further include a set of guidelines to be used as an aid in the selection of an optimal combination of detection device 10 and chemical indicator 12 for a given set of patient and/or environmental factors.

Therefore, the present invention provides a method and system for detecting pancreatic trauma, the method including positioning a detection device in contact with a patient's pancreas, or surrounding tissues or fluids, during a surgical operation, applying a chemical indicator to the detection device (such as after removing the detection device from the surgical area), and detecting a reaction that is indicative of enzyme release. The method is customizable to the patient by the operator to increase the likelihood, consistency, and accuracy of detecting a reaction that is indicative of enzyme release caused by injury to the patient's pancreas. Increasing the likelihood of detecting pancreatic injuries may decrease significant morbidity and mortality in patients.

Changes and modifications in the specifically described embodiments can be carried out without departing from the principles of the present invention which is intended to be limited only by the scope of the appended claims, as interpreted according to the principles of patent law including the doctrine of equivalents.

The invention claimed is:

1. A method of detecting pancreatic trauma, said method comprising:
   positioning an absorbent detection device into contact with an outer surface of a pancreas during a surgical operation, wherein an outer surface of the absorbent detection device is coated or impregnated with a first chemical reactant that is reactive with a pancreatic enzyme;
   removing the absorbent detection device from the outer surface of the pancreas;
   applying a chemical indicator containing a second chemical reactant to the outer surface of the absorbent detection device, wherein a product of the second chemical reactant with the first chemical reactant has a color that is visibly distinguishable from each of (i) a color of the first chemical reactant, (ii) a color of the pancreatic enzyme, and (iii) a color of a product of the first chemical reactant with the pancreatic enzyme; and
   detecting trauma to the pancreas via the absence, at the outer surface of the absorbent detection device, of the color of the product of the first and second chemical reactants.

2. The method of claim 1, wherein the absorbent detection device comprises a surgical pad or sponge.

3. The method of claim 1, wherein the first chemical reactant comprises starch and the second chemical reactant comprises iodine.

4. The method of claim 3, wherein the chemical indicator comprises povidone-iodine.

5. The method of claim 1, wherein said applying the chemical indicator comprises spraying the chemical indicator in liquid form onto the outer surface of the absorbent detection device.

6. The method of claim 1, further comprising providing a kit containing two or more of the absorbent detection devices and two or more of the chemical indicators.

7. A system for detecting pancreatic trauma, said system comprising:
   a deformable absorbent detection device having an outer surface with a surface color, said deformable absorbent detection device configured to be placed into contact with an outer surface of a pancreas;
   a first chemical reactant that is reactive with a pancreatic enzyme, wherein said first chemical reactant is applied to said outer surface of said deformable absorbent detection device;
   a second chemical reactant that is reactive with said first chemical reactant to produce a product color that is different from the surface color; and
   a liquid dispenser operable to contain and selectively dispense said second chemical reactant onto said outer surface of said deformable absorbent detection device;
   wherein contact of said second chemical reactant with said first chemical reactant along said outer surface of said deformable absorbent detection device causes the product color to form on said outer surface of said deformable absorbent detection device, and wherein absence of the product color along a portion of said outer surface of said deformable absorbent detection device is indicative of the presence of the pancreatic enzyme at said portion of said outer surface of said deformable absorbent detection device.

8. The system of claim 7, wherein said detection device comprises a deformable absorbent surgical pad or a sponge.

9. The system of claim 7, wherein said first chemical reactant comprises starch and said second chemical reactant comprises iodine.

10. The system of claim 9, wherein said second chemical reactant comprises povidone-iodine.

11. The system of claim 7, wherein said liquid dispenser comprises a sprayer.

12. A kit for detecting pancreatic trauma, said kit comprising:
   a plurality of absorbent detection devices each configured to be placed into contact with an outer surface of a pancreas and having an outer surface with a surface color, and a first chemical reactant applied to said outer surfaces, wherein said first chemical reactant is reactive with a pancreatic enzyme;
   a plurality of disposable packages each containing a respective one of said absorbent detection devices; and
   a liquid dispenser containing a second chemical reactant that is reactive with said first chemical reactant to produce a product color that is different from the surface color, wherein said liquid dispenser is operable to contain and selectively dispense said second chemical reactant onto said outer surface; and
   wherein contact of said second chemical reactant with said first chemical reactant along said outer surfaces of said absorbent detection device causes the product color to form on said outer surfaces of said absorbent detection devices, and wherein absence of the product color along a portion of said outer surface of each of said absorbent detection devices is indicative of the presence of the pancreatic enzyme at said portion of said outer surface of each of said absorbent detection devices.

13. The kit of claim 12, wherein said absorbent detection devices comprise surgical pads or sponges.

14. The kit of claim 12, wherein said first chemical reactant comprises starch and said second chemical reactant comprises iodine.

15. The kit of claim 14, wherein said second chemical reactant comprises povidone-iodine.

16. The kit of claim 12, wherein said liquid dispenser comprises a sprayer.

* * * * *